US011001607B2

(12) United States Patent
Peschard et al.

(10) Patent No.: US 11,001,607 B2
(45) Date of Patent: May 11, 2021

(54) PEPTIDE, COMPOSITION COMPRISING SAID PEPTIDE AND USES THEREOF, IN PARTICULAR COSMETIC USES

(71) Applicant: Sederma, Le Perray en Yvelines (FR)

(72) Inventors: Olivier Peschard, Rambouillet (FR); Anne Doucet, Rambouillet (FR); Richard Leroux, Faverolles (FR); Philippe Mondon, Montrouge (FR)

(73) Assignee: Sederma, Le Perray en Yvelines (FR)

( * ) Notice: Subject to any disclaimer, the term of this patent is extended or adjusted under 35 U.S.C. 154(b) by 106 days.

(21) Appl. No.: 16/307,548

(22) PCT Filed: Jun. 13, 2017

(86) PCT No.: PCT/EP2017/064439
§ 371 (c)(1),
(2) Date: Dec. 6, 2018

(87) PCT Pub. No.: WO2017/216177
PCT Pub. Date: Dec. 21, 2017

(65) Prior Publication Data
US 2019/0153030 A1 May 23, 2019

(30) Foreign Application Priority Data
Jun. 14, 2016 (FR) .................................... 1655468

(51) Int. Cl.
*C07K 5/09* (2006.01)
*A61Q 1/12* (2006.01)
*A61K 8/64* (2006.01)
*A61Q 19/08* (2006.01)
*C07K 7/06* (2006.01)

(52) U.S. Cl.
CPC .............. *C07K 5/0815* (2013.01); *A61K 8/64* (2013.01); *A61Q 1/12* (2013.01); *A61Q 19/08* (2013.01); *C07K 7/06* (2013.01)

(58) Field of Classification Search
None
See application file for complete search history.

(56) References Cited

U.S. PATENT DOCUMENTS

| 7,507,719 | B2 | 3/2009 | Pinel et al. | |
| 2010/0209427 | A1* | 8/2010 | Li | C12Q 1/48 424/139.1 |

FOREIGN PATENT DOCUMENTS

| WO | 2005009456 A2 | 2/2005 |
| WO | 2009003283 A1 | 1/2009 |
| WO | 2009003284 A1 | 1/2009 |
| WO | 2013117573 A1 | 8/2013 |
| WO | 2014080376 A2 | 5/2014 |
| WO | 2015181688 A1 | 12/2015 |

OTHER PUBLICATIONS

Polevoda et al. ('The diversity of acetylated proteins' Genome Biology v3(5) 2002 pp. 1-6) (Year: 2002).*
Choi et al. ('Dermal stability and in vitro skin permeation of collagen pentapeptides (KTTKS and palmitoyl-KTTKS)' Biomolecules and Therapeutics v22(4) 2014 pp. 321-327) (Year: 2014).*
Gurard-Levin et al. ('Peptide arrays identify isoform-selective substrates for profiling endogenous lysine deacetylase activity' ACS Chemical Biology v5(9) 2010 pp. 863-873) (Year: 2010).*
International Search Report and Written Opinion for International Application No. PCT/EP2017/064439, dated Aug. 24, 2017—10 pages.

* cited by examiner

*Primary Examiner* — Ronald T Niebauer
(74) *Attorney, Agent, or Firm* — RatnerPrestia

(57) ABSTRACT

The peptide has from 3 to 10 amino acids comprising at least the sequence K*(Ac)GH or K*(Ac)HG and may further comprise an N-terminus modification, preferably an acylation, and/or a C-terminus modification; K* is selected from the group consisting of lysine, ornithine, diaminobutyric acid, diaminopropionic acid and a hydroxylated derivative thereof; K*(Ac) corresponds to a lysine, ornithine, diaminobutyric acid, diaminopropionic acid or a hydroxylated derivative thereof, acetylated on the amine of their lateral hydrocarbon chain. The two preferred peptides are Pal-K(Ac)GH and Pal-K(Ac)HG. This peptide can be used for a cosmetic treatment, in particular anti-aging, anti-wrinkle and fine lines, to improve the mechanical properties of the skin, firmness/tonicity/elasticity/flexibility, to increase the density and volume of the skin, for a restructuring, healing effect, and/or to fight stretch marks.

15 Claims, No Drawings

Specification includes a Sequence Listing.

PEPTIDE, COMPOSITION COMPRISING SAID PEPTIDE AND USES THEREOF, IN PARTICULAR COSMETIC USES

This application is the U.S. National Phase application of PCT International Application No. PCT/EP2017/064439, filed Jun. 13, 2017, which claims the benefit of priority of French Patent Application No. FR 1655468, filed Jun. 14, 2016, the contents of which are incorporated herein by reference in their entirety for all purposes.

TECHNICAL FIELD

The present invention relates to novel peptides, compositions comprising them and cosmetic uses of said peptides. It relates more particularly to peptides intended for the treatment of the skin and its appendages, of mammals, humans or animals.

It concerns the cosmetics industries (topical or oral), hygiene and personal care products and dermo-pharmacy.

BACKGROUND ART

Peptides have an important signal function and coordinate many biochemical processes. Therefore peptides have become essential and promising active ingredients, particularly in the cosmetics industry, where new compounds are constantly being sought to beautify the skin and its appendages, namely to improve their general condition.

The present inventors have been particularly interested in finding novel peptides having an activity on the main molecules constituting the dermal extracellular matrix (ECM) which in particular decrease with age, and more particularly active on the synthesis of collagen I, of elastin and hyaluronic acid, and also active on the synthesis of glycoproteins such as fibronectin.

The loss of density and thickness of the dermis are linked to a reduction in the syntheses of macro-molecules during aging by the dermal fibroblasts, the cells in charge of their manufacture. Collagen I is the most abundant protein in the dermis and is essential for having a firm skin.

Elastin is synthesized and secreted into the dermal extracellular space. It is the major component of up to 90% of the elastic fibers.

Fibronectin is a glycoprotein present in the extracellular matrix, and plays a key role in the adhesion of cells to the extracellular matrix. It can simultaneously bind to the cell and to other molecules of the extracellular matrix, such as collagen or another fibronectin molecule. For this purpose, the fibronectin molecules are assembled to form elastic adhesive fibers on the surface of many cells. This determines the mechanical properties (elasticity, suppleness and firmness) of the skin.

Hyaluronic acid is an essential component of the dermis. The interest of hyaluronic acid lies in its viscoelastic properties and its ability to capture water. Water thus fills the spaces between the fibers of collagen and elastin, in the dermis. This contributes to the suppleness of the skin and to prevent the formation of wrinkles. This substance decreases with age, skin dries and wrinkles.

The increase of collagen IV and laminins is also sought. It helps to restore/strengthen the dermis/epidermis (DEJ) junction. Collagen IV forms a two-dimensional network and is one of the major components of the dermis/epidermis junction. The laminins are also contained in the basal layer and participate in anchoring the surfaces of the cells to the basal lamina. Together, these two essential components of the DEJ ensure that the keratinocytes of the basal lamina are better anchored and contribute to maintain the suppleness of the epidermis.

The reduction of protein synthesis with age is felt at the DEJ level. Collagen IV is more fragmented and at the same time less produced, like laminins, which in some areas leads to altered DEJ and less good communication between melanocytes, keratinocytes and DEJ and less flexibility of the system. The interest in stimulating the synthesis of these two proteins therefore clearly appears.

Results on the beautifying and the general state of the skin will be obtained thanks to the stimulated synthesis of these molecules, in terms of mechanical properties: a more dense, replumped, firmer, more tonic, more flexible and elastic skin, the peptide having a healing, volumizing, repulping effect, and therefore an anti-wrinkle effect, and also regarding the imperfections of the complexion (more homogeneous color and more radiance).

Many peptides or mixtures of peptides having properties on the ECM and anti-aging applications have already been proposed, in particular by the Applicant, such as the Pal-KTTKS (SEQ ID NO: 1) marketed under the trademark MATRIXYL™, the mixture of Pal-GHK and Pal-GQPR (SEQ ID NO: 2) marketed under the trademark MATRIXYL 3000™ or more recently the Pal-KMO$_2$K marketed under the trademark MATRIXYL™ synthe'6 (MO$_2$ corresponding to a dioxygenated methionine). Other known peptides are mentioned below in the description.

The aim of the present invention is to propose still other peptides capable of improving the general condition of the skin and its appendages, and more particularly peptides that are active on the synthesis of the proteins of the ECM. Furthermore, the aim is to propose peptides that are sufficiently effective to be used alone or in combination, in proportions of a few ppm, and that they can be used in the form of a topical composition, in particular a cosmetic composition.

SUMMARY OF THE INVENTION

The present invention provides a peptide comprising from 3 to 10 amino acids including at least one peptide sequence K*(Ac)GH or a peptide sequence K*(Ac)HG and which may comprise an N-terminal and/or C terminal modification, wherein:

K* is selected from the group consisting of: lysine (Lys, K), ornithine (Orn), diaminobutyric acid (Dab), diaminopropionic acid (Dap) and hydroxylated derivative of lysine;

K*(Ac) corresponds to a lysine, ornithine, diaminobutyric acid, diaminopropionic acid or a hydroxylated derivative thereof, acetylated on the amine of their lateral hydrocarbon chain;

Said modification at the N-terminus is —CO—R$_1$ or —SO$_2$—R$_1$;

Said C-terminal modification is selected from the group consisting of —OR$_1$, —NH$_2$, —NHR$_1$ and —NR$_1$R$_2$; and R$_1$ and R$_2$ independently of one another are chosen from an alkyl, aryl, aralkyl, alkylaryl, alkoxy and aryloxy group, which may be linear, branched, cyclic, polycyclic, unsaturated, hydroxylated, carbonylated, phosphorylated and/or sulfurated, said group having from 1 to 24 carbon atoms and may have in its carbon skeleton an O, S and/or N heteroatom.

Conventionally, the N-terminus is that of the amino acid shown to the left of the peptide formula and the C-terminus is that of the amino acid shown to the right of the formula.

As can be seen in the table below, ornithine, diaminobutyric acid and diaminopropionic acid are lysine analogs according to the present invention, each comprising a side chain of 3, 2 and 1 atom(s) of carbon instead of 4 for lysine, and ending with an amine $NH_2$ function. The number of carbons playing the role of spacer more or less long. According to the invention, it is on this lateral amine function that an acetyl group —$(CO)CH_3$ is grafted.

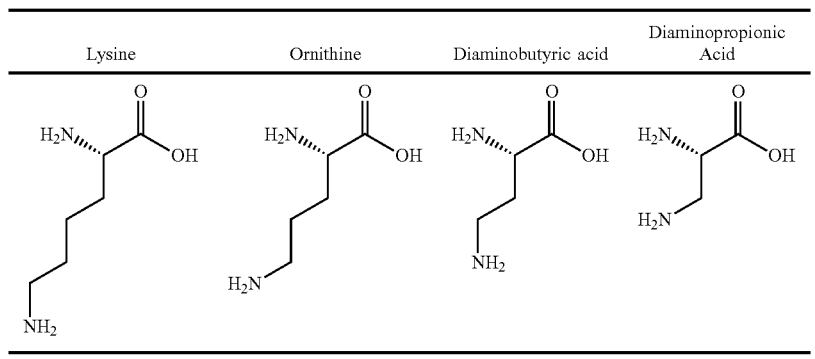

The hydroxyl derivatives of K* comprise a hydroxyl radical on the hydrocarbon side chain, such as, for example, the hydroxylysine of formula:

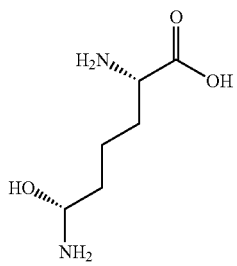

The amino acids of the peptide according to the invention other than those of the inventive sequences K*(Ac)HG and/or K*(Ac)GH may be chosen from the 20 natural amino acids or derivatives or analogs thereof, preferably chosen from lysine, histidine, glycine, alanine and an amino acid K* as defined according to the invention, more preferably glycine or alanine.

The peptide according to the invention can comprise several times the inventive sequence K*(Ac) HG and/or K*(Ac)GH.

Preferably according to the invention K* is a lysine, K*(Ac) corresponding therefore to an ε-acetylated lysine.

Preferably also, the peptide comprises either an N-terminus modification or a C-terminal modification corresponding to a group $R_1$ and/or $R_2$ as defined above preferably having 3 to 24 carbon atoms, in order to form a fatty chain and thus increasing the lipophilic character of the peptide and its penetrating capacity in the skin.

According to a preferred possibility, the peptide according to the invention:
Comprises at the C-terminus a short modification OMe, OEt and $NH_2$ or is free of modification (includes an OH terminus), more preferably free of modification; and At the N-terminal end, comprises a modification, preferably an acylation —CO—$R_1$, preferably with a group $R_1$ of 3 to 24 carbon atoms, and more preferably chosen from an octanoyl (C8), decanoyl (C10), lauryl (C12), myristoyl (C14), palmitoyl (C16), stearoyl (C18), biotinoyl, elaidyl, oleoyl and lipoyl.

According to another possibility, the peptide according to the invention:
Comprises at the C-terminus a modification, preferably —$OR_1$ with $R_1$ being an alkyl chain of 3 to 24 carbons; and At the N-terminus comprises a short modification $NHR_1$ where $R_1$ being an alkyl chain of 1 to 3 carbons or is free of modification (includes an $NH_2$-terminus), more preferably free of modification.

According to other preferred features, the peptide according to the invention is a small peptide comprising from 3 to 6 amino acids, more preferably including 3 amino acids corresponding to the sequence according to the invention K*(Ac)HG or the sequence K*(Ac)GH, that is to say corresponding to the tripeptides of formulas:

X-K*(Ac)GH-Z           (1)

X-K*(Ac)HG-Z          (2)

Wherein:
X corresponds, when present, to the N-terminus modification; and
Z corresponds, when present, to the C-terminus modification.

The preferred peptides according to the invention are Pal-K(Ac)HG and Pal-K(Ac)GH, corresponding to a palmitoyl modification at the N-terminus and free of modifications at the C-terminus (OH terminus).

The detailed description of in vitro tests given below shows that such peptides exhibit activity on the ECM marker molecules which are active from a few ppm and which can be used alone or as a mixture to improve the appearance and general condition of skin and its appendages, and in particular for the treatment and/or prevention of the signs of aging, and/or of imperfections of the skin and its appendages. The inventors have shown that the peptides according to the invention have in particular a pro-collagen activity.

Tests also show that the peptides have a higher activity than the corresponding sequence peptides comprising a non-acetylated K* amino acid.

The peptides according to the invention may be optically pure, or consist of the L or D isomers or a mixture thereof. The L isomers which are those present in the natural state may be preferred.

The peptides may be in the form of salts, in particular hydrochloric or acetic salts.

The present invention also covers derivatives (with modification and/or addition of a chemical function but without change in the carbon skeleton) and analogs (with modification and/or addition of a chemical function but additionally with a change in the carbon skeleton), complexes with other species such as a metal ion (eg copper, zinc, manganese, magnesium, and the like).

The present invention also provides a composition, in particular a topical composition, comprising at least one peptide according to the invention in a physiologically acceptable medium. Depending on the excipient and the peptide dosage, this composition will constitute, for example, a concentrated active ingredient or a less concentrated final composition intended directly for the user.

"Physiologically acceptable medium" means according to the present invention, without limitation, an aqueous or hydro-alcoholic solution, a water-in-oil emulsion, an oil-in-water emulsion, a micro-emulsion, an aqueous gel, an anhydrous gel, a serum, a dispersion of vesicles, or a powder.

"Physiologically acceptable" means that the compositions are suitable for topical or transdermal use, in contact with mucous membranes, appendages (nails, hairs, body hair), scalp and skin of mammals, particularly human, compositions which may be ingested, or injected into the skin, without risk of toxicity, incompatibility, instability, allergic response, and others. This "physiologically acceptable medium" forms what is commonly called the excipient of the composition.

The peptides of the invention can be solubilized in a lipophilic or hydrophilic matrix with optionally a solubilizer, according to the envisaged use.

The peptide(s) may be combined with other active ingredients at effective concentrations that can act synergistically or additionnaly for reinforcing and achieveing the desired effects described for the invention, such as the following agents: anti-aging, anti-fine lines and wrinkles, lightening, pro-pigmenting, hydrating, moisturizing, humectant, slimming, exfoliating, anti-acne, anti-redness, anti-inflammatories, anti-oxidant/radical scavengers, acting on brightness of complexion, anti-glycation, volumizing, restructuring, anti-carbonylation, dermo-relaxing, anti-hair regrowth, acting on stratum corneum, dermal-epidermal junction, HSP protein production, firmness, elasticity and tone of skin, hair growth (eyelashes and eyebrows), eye contours (dark circles and under eye bags), promoting blood circulation, other peptides, vitamins etc. These active ingredients may be obtained from plant materials, such as classical plant extracts or products of plant cell culture or fermentation.

More specifically, the peptides according to the invention may be combined with at least one of compounds selected from compounds of the vitamin B3, compounds such as niacinamide or tocopherol, retinoid compounds such as retinol, hexamidine, α-lipoic acid, resveratrol or DHEA, hyaluronic acid, other peptides, in particular N-acetyl-Tyr-Arg-O-hexadecyl ester, Pal-VGVAPG (SEQ ID NO: 3), Pal-KTTKS (SEQ ID NO: 1), Pal-GHK, Pal-KMO2K and Pal-GQPR (SEQ ID NO: 2), which are widely used active ingredients in topical cosmetic or dermopharmaceutical compositions.

The composition according to the invention may be applied to the face, body, neckline, scalp, hair, eyelashes, body hair, in whatever form or carriers known to those skilled in the art, in particular in the form of solution, dispersion, emulsion, paste, or powder, individually or as a premix or in vehicles individually or as a premix in vectors such as macro-, micro-, or nano-capsules, macro-, micro- or nano-spheres, liposomes, oleosomes or chylomicrons, macro-, micro-, or nanoparticles or macro-, micro- or nano-sponges, micro- or nano-emulsions or adsorbed on organic polymer powders, talcs, bentonites, spores or exines, and other inorganic or organic supports.

In cosmetics, applications can particularly be offered in skincare ranges for the face, body, hair and body hairs, and in make-up ranges, including for eyebrows and eyelashes.

In general, the peptides according to the present invention may be used in any form, in a form bound to or incorporated in or absorbed in or adsorbed on macro-, micro-, and nanoparticles, or macro-, micro-, and nano-capsules, for the treatment of textiles, natural or synthetic fibers, wools, and any materials that may be used for clothing or underwear for day or night intended to come into contact with the skin, handkerchiefs or cloths, to exert their cosmetic effect via this skin/textile contact and to permit continuous topical delivery.

The CTFA («International Cosmetic Ingredient Dictionary & Handbook» (16-th Ed. 2016) published by «the Personal Care Products council», ex-«the Cosmetic, Toiletry, and Fragrance Association, Inc.», Washington, D.C.), describes a non-limited wide variety of cosmetic and pharmaceutical ingredients commonly used in the skin care industry, which are suitable for use as additional ingredients in the compositions according to the present invention.

Further additional skin care actives that are particularly useful can be found in the commercial literature of Sederma and on the website www.sederma.com.

The following commercial actives can also be mentioned, as examples: betaine, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Argireline™ (commercial name for the acetyl hexapeptide-3 of Lipotec), spilanthol or an extract of *Acmella oleracea* known under the commercial name Gatuline Expression™, an extract of *Boswellia serrata* known under the commercial name Boswellin™, Deepaline PVB™ (Seppic), Syn-AKE™ (Pentapharm), Ameliox™, Bioxilift™ (Silab), PhytoCellTec™ Argan (Mibelle), Papilactyl D™ (Silab), Preventhelia™ (Lipotec), or the following active ingredients proposed by Sederma: Subliskin™ Venuceane™, Moist 24™, Vegesome Moist 24™, Essenskin™, Juvinity™, Revidrat™ Resistem™, Chronodyn™, Kombuchka™, Chromocare™, Calmosensine™, Glycokin factor S™ Biobustyl™, Idealift™, Ceramide 2™, Ceramide A2™, Ceramide HO3™, Legance™ Intenslim™, Prodizia™, Beautifeye™, Pacifeeff, NG-shea butter unsaponifiables (natural grade), Zingerslim™, Meiritage™, Senestem™, Sebuless™, Majestem™, Apiscalp™, Rubistem™ Citystem™, Neonyca™ or mixture thereof.

Among plant extracts (in the form of classical extracts or prepared in vitro) which can be combined with the peptide(s) of the invention, there may more particularly be mentioned extracts of Ivy, in particular English Ivy (*Hedera Helix*), of *Bupleurum chinensis*, of *Bupleurum falcatum*, of arnica (*Arnica montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum perforatum*), of butcher's-broom (*Ruscus aculeatus* L), of European meadowsweet (*Filipendula ulmaria* L), of big-flowered Jarva tea (*Orthosiphon stamincus berth*), of artichoke (*Cynara scoly-*

*mus*), of algae (*Fucus vesiculosus*), of birch (*Betula alba*), of green tea, of cola nuts (*Cola nipida*), of horse-chestnut, of bamboo, of *Centella asiatica*, of heather, of focus, of willow, of mouse-ear, of escine, of cangzhu, of *chrysanthellum indicum*, of the plants of the *Armeniacea* genus, *Atractylodis platicodon, Sinnomenum, Pharbitidis, Flemingia*, of *Coleus* such as *C. forskohlii, C. blumei, C. esquirolii, C. scutellaroides, C. xanthantus* and *C. barbatus*, such as the extract of root of *Coleus barbatus*, extracts of *Ballote*, of *Guioa*, of *Davallia*, of *Terminalia*, of *Barringtonia*, of *Trema*, of *Antirobia, Cecropia, Argania, Dioscoreae* such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi, aloe vera*, plant containing sterols (e.g., phytosterol), Manjistha (extracted from plants of the genus *Rubia*, particularly *Rubia cordifolia*), and Guggal (extracted from plants of the genus *Commiphora*, particularly *Commiphora mukul*), kola extract, chamomile, red clover extract, Piper methysticum extract (Kava Kava™ from Sederma), *Bacopa monieri* extract (Bacocalmine™ from Sederma) and sea whip extract, extracts of *Glycyrrhiza glabra*, of mulberry, of *Melaleuca* (tea tree), of *Larrea divaricata*, of *Rabdosia rubescens*, of *Euglena gracilis*, of *Fibraurea recisa hirudinea*, of *Chaparral sorghum*, of sun flower extract, of *Enantia chlorantha*, of Mitracarpe of *Spermacocea* genus, of *Buchu barosma*, of *Lawsonia inermis* L., of *Adiantium capillus-veneris* L., of *Chelidonium majus*, of *Luffa cylindrica*, of Japanese Mandarin (*Citrus reticulata blanco* var. *unshiu*), of *Camelia sinensis*, of *Imperata cylindrica*, of *Glaucium Flavum*, of *Cupressus Sempervirens*, of *Polygonatum multiflorum*, of *loveyly hemsleya*, of *Sambucus nigra*, of *Phaseolus lunatus*, of *Centaurium*, of *Macrocystis pyrifera*, of *Tumera diffusa*, of *Anemarrhena asphodeloides*, of *Portulaca pilosa*, of *Humulus lupulus*, of *Coffea Arabica*, of *Ilex paraguariensis*, or of *Globularia cordifolia*, of *Albizzia julibrissin*, of *Oxydendron arboretum*, of *Zingimber Zerumbet Smith*, of *Astragalus membranaceus*, of *Atractylodes macrocephalae*, of *Plantago lanceolata*, of *Leontopodium alpinum* (or eldelweiss), of *Mirabilis jalapa* or of *Apium graveolens* or of *Marrubium vulgare* or of orchids.

The compositions of the present invention may include one or more peptides, including, without limitation, the di-, tri-, tetra-, penta- and hexapeptides and their derivatives. According to a particular embodiment, the concentration of the additional peptide, in the composition, ranges from $1 \times 10^{-7}\%$ and 20%, preferably from $1 \times 10^{-6}\%$ and 10%, preferably between $1 \times 10^{-5}\%$ and 5% by weight.

According to the present invention, the term "peptide" refers to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides and which are found in nature, and/or are commercially available.

Suitable dipeptides for use herein include but are not limited to Carnosine (beta-AH), YR, VW, NF, DF, KT, KC, CK, KP, KK, TT, PA, PM or PP.

Suitable tripeptides for use herein include, but are not limited to RKR, HGG, GHK, GGH, GHG, KFK, KAvaK, KβAK, KAbuK, KAcaK, KPK, KMOK, KMO2K, PPL, PPR, SPR, QPA, LPA or SPA.

Suitable tetrapeptides for use herein include but are not limited to RSRK (SEQ ID NO: 4), GQPR (SEQ ID NO: 5) or KTFK (SEQ ID NO: 6), KTAK (SEQ ID NO: 7), KAYK (SEQ ID NO: 8) or KFYK (SEQ ID NO: 9).

Suitable pentapeptides include, but are not limited to KTTKS (SEQ ID NO: 10). Suitable hexapeptides include but are not limited to GKTTKS (SEQ ID NO: 11) and VGVAPG (SEQ ID NO: 12).

Other suitable peptides for use herein include, but are not limited to: lipophilic derivatives of peptides, preferably palmitoyl derivatives, and metal complexes as aforementioned (e.g. copper complex of the tripeptide HGG). Preferred dipeptide include for example N-Palmitoyl-beta-Ala-His, N-Acetyl-Tyr-Arg-hexadecylester (Calmosensine™, Idealift™ from Sederma). Preferred tripeptide derivatives include for example N-Palmitoyl-Gly-Lys-His and Pal-Gly-His-Lys (Pal-GKH and Pal-GHK from Sederma), the copper derivative of HGG (Lamin™ from Sigma), Lipospondin (N-Elaidoyl-KFK) and its analogs of conservative substitution, N-Acetyl-RKR-NH$_2$ (Peptide CK+), N-Biot-GHK (from Sederma), Pal-KAvaK, Pal-KβAlaK, Pal-KAbuK, Pal-KAcaK, Pal-KMO$_2$K (Matrixyl Synthe'6™ from Sederma) and derivatives thereof. The anti-aging tripeptides of general formula X-Pro*-Pro*-Xaa-Y described in the patent application WO2015181688 can also be cited here, with Xaa selected from Leu, Arg, Lys, Ala, Ser, and Asp, at the N-terminus end, X selected from H, —CO—R$_1$ and —SO$_2$—R$_1$ and at the C-terminal end Y is chosen from OH, OR$_1$, NH$_2$, NH$_{R1}$ or NR$_1$R$_2$, R$_1$ and R$_2$ being chosen, independently of one another, in the group comprising an aryl, aryl, aralkyl, alkylaryl, alkoxy and aryloxy group which can be linear, branched, cyclic, polycyclic, unsaturated, hydroxylated, carbonylated, phosphorylated and/or sulfurated, said group possessing in its backbone a heteroatom, in particular O, S and/or N, and Pro* corresponding to Proline, an analog or a derivative thereof; including, for example, Myr-PPL-OH and Myr-PPR-OH.

Also suitable herein are the pro-pigmenting and/or pro-ECM dipeptides and tripeptides of general formula X-(Xaa1)n-Pro*-Xaa2-Y described in the patent application WO 2014/080376, with n=0, 1 or 2, Xaa1 being a hydrophobic amino acid selected from Ala, Val, Met, Leu, Iso, Phe, Pro, and analogs or derivatives thereof; or a polar amino acid selected from Ser, Thr, Tyr, Asp, Glu and derivatives and analogues thereof; and when n=2, the two amino acids Xaa1 may be identical or different; Xaa2 being a hydrophobic amino acid selected from Ala, Val, Met, Leu, Iso, Phe, and analogs or derivatives thereof; a basic amino acid selected from Arg, Lys, His, and derivatives and analogues thereof; at the N-terminus end of the peptide, X being selected from H, —CO—R$_1$ and —SO$_2$—R$_1$; at the C-terminus end of the peptide, Y being selected from OH, OR$_1$, NH$_2$, NHR$_1$ or NR$_1$R$_2$, R$_1$ and R$_2$ being, independently of one another, chosen from an alkyl, aryl, aralkyl, alkylaryl, alkoxy and aryloxy group, which may be linear, branched, cyclic, polycyclic, unsaturated, hydroxylated, carbonylated, phosphorylated and/or sulfurated, said group possessing in its backbone a heteroatom, especially O, S and or N; Pro* corresponding to Proline, an analog or a derivative thereof; which includes, for example, the peptides Pal-SPR-OH, Pal-PA-OH, Pal-PA-OH, Pal-QPA-OH, Pal-LPA-OH, Myr-SPA-OH and Pal-PP-OH.

Suitable tetrapeptide derivatives for use according to the present invention include, but are not limited to, N-Pal-GQPR (SEQ ID NO: 2) (from Sederma), Pal-KTFK (SEQ ID NO: 13) or Ela KTFK (SEQ ID NO: 14), Ela-KTAK (SEQ ID NO: 15), Ela-KAYK (SEQ ID NO: 16) or Ela-KFYK (SEQ ID NO: 17). Suitable pentapeptide derivatives for use herein include, but are not limited to, Pal-KTTKS (SEQ ID NO: 1) (available as Matrixyl™ from Sederma), N-Pal-Tyr-Gly-Gly-Phe-X (SEQ ID NO: 18) with X being Leu or Pro, N-Pal-His-Leu-Asp-Ile-Ile-X with X being Trp, Phe, Tyr, Tic, 7-hydroxy-Tic or Tpi (SEQ ID NO: 19), or mixture thereof. Hexapeptide derivatives comprise the N-Pal-VGVAPG (SEQ ID NO: 3), Pal-GKTTKS (SEQ ID NO: 20) and their derivatives. The mixture of Pal-GHK and Pal-GQPR (SEQ ID NO: 2) (Matrixyl™ 3000, Sederma) can also be mentioned.

The preferred compositions commercially available containing a tripeptide or a derivative include Biopeptide-CL™, Maxilip™, Biobustyl™, Procapil™ and Matrixyl™ synthe'6™ of Sederma. The compositions commercially available preferred sources of tetrapeptides include Rigin™, Eyeliss™, Matrixyl™ Reloaded and Matrixyl 3000™ which contain between 50 and 500 ppm of Pal-GQPR (SEQ ID NO: 2) and an excipient, proposed by Sederma.

The following marketed peptides can be mentioned as well as additional active ingredients:
  Vialox™ (INCI name=Pentapeptide-3 (synthetic peptide comprising alanine, arginine, isoleucine, glycine and proline)), Syn-ake™ (β-Ala-Pro-Dab-NH-Bzl) or Syn-Coll™ (Pal-Lys-Val-Lys-OH) marketed by DSM;
  Argireline™ (Ac-Glu-Glu-Met-Gln-Arg-Arg-NH$_2$ (INCI name=Acetyl hexapeptide-3) (SEQ ID NO: 21), Leuphasyl™ (Tyr-D-Ala-Gly-Phe-Leu) (SEQ ID NO: 22), Aldenine™ (Gly-His-Lys), Trylagen™ (INCI name=Pseudoalteromonas Ferment Extract, Hydro lyzed Wheat Protein, Hydro lyzed Soy Protein, Tripeptide-10 Citrulline (reaction product of Citrulline and Tripeptide-10 (synthetic peptide constituted of aspartic acid, isoleucine and lysine)), Tripeptide-1), Eyeseryl™ (Ac-(-Ala-His-Ser-His)(SEQ ID NO: 23), Serilesine™ (Ser-Ile-Lys-Val-Ala-Val) (SEQ ID NO: 24) or Decorinyl™ (INCI name: Tripeptide-10 Citrulline=reaction product of Citrulline and Tripeptide-10 (synthetic peptide constituted of aspartic acid, isoleucine and lysine) marketed by Lipotec;
  Collaxyl™ (Gly-Pro-Gln-Gly-Pro-Gln (SEQ ID NO: 25)) or Quintescine™ (Cys-Gly) marketed by Ashland;
  Cytokinol™ LS (casein hydrolysate) marketed by BASF;
  Kollaren™ (Gly-His-Lys), IP2000™ (Pal-Val-Tyr-Val) or Meliprene™ (INCI name=Monofluoroheptapeptide-1: reaction product of acetic acide and a synthetic peptide comprising arginine, glycine, glutamic acid, histidine, norleucine, p-fluorophenylalanine and tryptophan) marketed by l'Institut Europeen de Biologie Cellulaire;
  Neutrazen™ (Pal-His-D-Phe-Arg-NH$_2$) marketed by Innovations; or
  BONT-L-Peptide™ (INCI name=Palmitoyl Hexapeptide-19: reaction product of palmitic acid and Hexapeptide-19 (synthetic peptide constituted of asparagine, aspartic acid, lysine and methionine), Timp-Peptide™ (INCI name=Acetyl Hexapeptide-20: reaction product obtained by acetylation of Hexapeptide-20 (synthetic peptide constituted of alanine, glycine, lysine, valine and proline) or ECM Moduline™ (INCI name =Palmitoyl Tripeptide-28: reaction product of palmitic acid and Tripeptide-28 (synthetic peptide constituted of arginine, lysine and phenylalanine) marketed by lnfinitec Activos.

The present invention proposes the use of at least one peptide according to the invention or of a composition comprising it, as recited above, for a non-therapeutic cosmetic treatment to improve the overall condition of the skin and/or of its appendages and to treat its imperfections.

Preferably according to the invention, the treatment is topical.

The peptide according to the invention is more particularly recommended according to the invention for an anti-aging treatment, in particular a treatment:
  of wrinkles and fine lines; and/or
  for improving the mechanical properties of the skin: firmness, tone, elasticity and/or suppleness; and or
  for healing; and/or
  for increasing the density and volume of the skin (volumizing, repulping and/or restructuring effect); and/or
  for fighting stretch marks; and/or
  for improving the homogeneity and/or radiance of complexion.

Other applications can be envisaged for the peptides according to the invention (alone or in combination), for example moisturizing, slimming, detoxifying, anti-glycation, anti-free radicals, tensors, anti-fatigue, anti-under eye bags and/or calming, action on the growth of hair, action on the pigmentation, on the scalp, etc. for preventive or curative purposes.

The present invention covers a cosmetic, non-therapeutic topical treatment method for improving the appearance and general condition of the skin and its appendages, including the topical application to the skin of a subject in need thereof of an effective amount of a peptide or a mixture of peptides according to the invention or of a composition according to the invention comprising said peptide or mixture of peptides, the peptides being as recited above according to the invention.

"Topical treatment" or "topical use" means according to the invention an application which is intended to act at the place where it is applied: skin, mucosa, appendages.

The composition comprising the peptide(s) according to the invention can be applied locally to the targeted zones.

For the use according to the invention, the effective amount of the active ingredient in the composition, that is to say its dosage, depends on various factors, such as the age, the condition of the skin of the patient, etc. An effective amount means a non-toxic amount enough to achieve the desired effect.

In a cosmetic composition according to the invention, the peptides to be present in an effective amount can be present in proportions of between 0.000001% and 15% relative to the total weight of the composition, preferably between 0.00001% and 5%, more preferably between 0.0001% and 0.01% (between 1 and 100 ppm) for a topical cosmetic application, depending on the purpose of the composition and the desired effect more or less pronounced. The peptides may be present in the compositions according to the invention in variable proportions, in equivalent amounts, or conversely in different proportions.

All percentages and ratios used herein are by weight of the total composition and all measurements are made at 25° C. unless it is otherwise specified.

For example, for a face cosmetic treatment, the European Cosmetics Directive has set a standard amount for applying a cream of 2.72mg/cm$^2$/day/person, and for a body lotion of 0.5mg/cm$^2$/day/person, which gives a standard indication of the dosages per day and person for a cosmetic treatment according to the invention.

According to other specific features, the cosmetic treatment method according to the invention can be combined with one or more other treatment methods targeting the skin such as lumino-therapy, heat or aromatherapy treatments.

According to the invention, devices with several compartments or kits may be proposed to apply the method described above which may include for example and non-restrictively, a first compartment containing a composition comprising a peptide of the invention, and in a second compartment a composition containing another active ingredient and/or excipient, the compositions contained in the said first and second compartments in this case being considered to be a combination composition for simultaneous, separate or stepwise use in time.

The treatment method according to the invention is more particularly adapted to slow degradations of the molecules of the dermal extracellular matrix and/or to act on the DEJ via the stimulation of collagen IV and/or laminins.

Other applications can be envisaged for the peptides according to the invention (alone or in combination), for example moisturizing, slimming, detoxifying, anti-glycation, anti-free radicals, tensing, anti-fatigue, for treating under eye bags and/or dark circles, calming, for an action on hair growth, on the radiance of the complexion, on pigmentation, on the scalp, etc. for preventive or curative purposes.

DETAILED DESCRIPTION

The following examples describe and illustrate certain aspects of the invention.

A) Example of Manufacturing of a Peptide According to the Invention: the Pal-K(Ac)HG The peptide Pal-K(Ac)HG is prepared by peptide synthesis. The glycine is coupled with a resin via its terminal acid function (with a coupling agent for example DCC (diclyclohexylcarbodiimide)/NHS (N-hydroxysuccinimide) or HBTU (2-(1H-benzotriazol-1-yl) 3,3-tetramethyluronium hexafluorophosphate)/HOBT (1-hydroxy-benzotriazole)). The glycine thus protected is then reacted with a derivative of histidine in the presence of a coupling agent, and then the same operation is carried out to add the previously acetylated lysine. The latter is then acylated on its amine function with an activated palmitic acid derivative (palmitoyl chloride for example) in the presence of a base. After cleavage of the peptide resin, precipitation of the peptide, washing and drying, the acetylated palmitoyl-lysyl-glycyl-histidine product is obtained in solid form.

This procedure is applicable to obtain Pal-K(Ac)HG by initially inverting glycine and histidine.

B) Preparation of a Composition According to the Invention Comprising the Pal-K(Ac)HG Peptide of l'example A) or the Pal-K(Ac)GH peptide Starting Materials:

The pure peptide, synthesized according to the synthesis method explained above;

Excipient: mixture of fatty esters, chosen in order to form an oily matrix, for example intended to form a anhydrous composition water for the subsequent formulation of anhydrous cosmetic compositions.

Procedure: The peptide is mixed with the excipient and stirred gently and heated until solubilization and total clarity.

C) In Vitro Tests

The peptides according to the invention have a number of remarkable effects presented below. Peptides prepared according to A) above and dissolved in an excipient were in vitro tested and showed activities which are presented hereinafter.

1) ELISA Assays

Protocol

Cultured normal human fibroblasts (NHF) are brought into contact with the test products or their excipient (negative control) for 72 hours. At the end of the contact, the culture supernatants are removed and the syntheses of the dermal macromolecules are estimated by ELISA assays. An estimation of the cell viability is carried out by Hoechst assay and makes it possible to weigh the data obtained.

Results for the Pal-K(Ac)HG

TABLE 1

| Collagen I | % change/control (significance - Student test) | |
|---|---|---|
| Concentration | Pal-KHG | Pal-K(Ac)HG |
| 7 ppm | / | +40 ($p < 0.05$) |
| 10 ppm | +41 ($p < 0.05$) | +138 ($p < 0.01$) |
| 12.5 ppm | +123 ($p < 0.01$) | / |
| 15 ppm | / | +241 ($p < 0.01$) |

TABLE 2

| Collagen IV | % change/control (significance-Student test) | |
|---|---|---|
| Concentration | Pal-KHG | Pal-K(Ac)HG |
| 10 ppm | +45 ($p < 0.01$) | +67 ($p < 0.01$) |
| 12.5 ppm | +141 ($p < 0.01$) | / |
| 15 ppm | / | +155 ($p < 0.01$) |

TABLE 3

| Fibronectin | % change/control (significance-Student test) | |
|---|---|---|
| Concentration | Pal-KHG | Pal-K(Ac)HG |
| 10 ppm | +128 ($p < 0.01$) | +128 ($p < 0.01$) |

TABLE 4

| Hyaluronic acid | % change/control (significance-Student test) | |
|---|---|---|
| Concentration | Pal-KHG | Pal-K(Ac)HG |
| 3 ppm | −14 (nsd) | +259 ($p < 0.01$) |
| 7 ppm | +4 (nsd) | +142 ($p < 0.01$) |
| 10 ppm | +11 (nsd) | +123 ($p < 0.01$) |
| 12.5 ppm | +33 ($p < 0.05$) | +119 ($p < 0.01$) | nsd: non significant data

The results show that the Pal-K(Ac)HG peptide according to the invention stimulates the synthesis of collagens I and IV, fibronectin and hyaluronic acid on normal human fibroblasts at concentrations of a few ppm and in significant proportions. The results also show that the Pal-K(Ac)HG peptide according to the invention is advantageously more active than its non-acetylated version on lysine (Pal-KHG) for collagens I and IV, and hyaluronic acid very largely from 3 ppm, whereas there is no decreased activity on fibronectin.

Results for the Pal-K(Ac)GH

TABLE 5

| Collagen I | % change/control (significance-Student test) | |
|---|---|---|
| Concentration | Pal-KGH | Pal-K(Ac)GH |
| 3 ppm | +81 ($p < 0.01$) | +71 ($p < 0.01$) |
| 5 ppm | / | +75 ($p < 0.01$) |
| 7 ppm | +69 ($p < 0.05$) | +119 ($p < 0.01$) |
| 10 ppm | +123 ($p < 0.01$) | / |

TABLE 6

| Collagen IV | % change/control (significance-Student test) | |
| --- | --- | --- |
| Concentration | Pal-KGH | Pal-K(Ac)GH |
| 10 ppm | +59 (p < 0.01) | +80 (p < 0.01) |

TABLE 7

| Fibronectin | % change/control (significance-Student test) | |
| --- | --- | --- |
| Concentration | Pal-KGH | Pal-K(Ac) GH |
| 10 ppm | +45 (p < 0.01) | / |
| 12.5 ppm | / | +35 (p < 0.01) |

TABLE 8

| Elastin | % change/control (significance-Student test) | |
| --- | --- | --- |
| Concentration | Pal-KGH | Pal-K(Ac) GH |
| 7 ppm | −62 (p < 0.05) | / |
| 10 ppm | / | +207 (p < 0.01) |

TABLE 9

| Hyaluronic acid | % change/control (significance-Student test) | |
| --- | --- | --- |
| Concentration | Pal-KGH | Pal-K(Ac)GH |
| 3 ppm | / | +111 (p < 0.01) |
| 7 ppm | +113 (p < 0.05) | +244 (p < 0.01) |
| 10 ppm | +118 (p < 0.05) | +260 (p < 0.01) |
| 12.5 ppm | / | +437 (p < 0.01) |

The results show that the peptide Pal-K(Ac)GH according to the invention stimulates the synthesis of collagens I and IV, fibronectin, elastin and hyaluronic acid on normal human fibroblasts at concentrations of a few ppm and in significant proportions. The results also show that the Pal-K(Ac)GH peptide according to the invention is advantageously more active than its non-acetylated version on lysine (the Pal-KGH) for collagens I (at 7 ppm) and IV (at 10 ppm), elastin above 10 ppm, and hyaluronic acid very largely from 3 ppm.

2) Immunofluorescence Assays

Protocol

Normal Human Fibroblasts (NHF) are grown for 24 h. The cells are placed in contact with the test products or their excipient at different concentrations for 6 days for collagen I or 14 days for elastin (DMEMc 5% FCS). The synthesis of collagen I and elastin produced by the cells in the form of extracellular matrix is then quantified by immuno-marking on the attached layers. A count of the Hoechst-labeled nuclei is performed in parallel in order to have an estimate of the viability and to weight the data.

Results

TABLE 10

| Collagen I | % change/control (significance-Student test) | |
| --- | --- | --- |
| Concentration | Pal-KHG-OH | Pal-K(Ac)HG-OH |
| 3 ppm | +20 (p < 0.05) | +42 (p < 0.01) |
| 7 ppm | +34 (p < 0.01) | / |
| 10 ppm | / | +45 (p < 0.01) |
| 15 ppm | / | +120 (p < 0.01) |

TABLE 11

| Collagen IV | % change/control (significance-Student test) | |
| --- | --- | --- |
| Concentration | Pal-KHG-OH | Pal-K(Ac)HG-OH |
| 10 ppm | +217 (p < 0.01) | +231 (p < 0.01) |

TABLE 12

| Elastin | % change/control (significance-Student test) | |
| --- | --- | --- |
| Concentration | Pal-KHG-OH | Pal-K(Ac)HG-OH |
| 3 ppm | / | +326 (p < 0.01) |
| 7 ppm | / | +438 (p < 0.01) |
| 10 ppm | / | +221 (p < 0.01) |

The results confirm that the Pal-K(Ac)HG peptide according to the invention stimulates the synthesis of collagens I and IV and show that it strongly stimulate the synthesis of elastin. The results also confirm that the Pal-K(Ac)HG peptide according to the invention is advantageously more active than its non-acetylated version on lysine (Pal-KHG) for collagens I and IV and advantageously exhibits very high activity on the elastin whereas the non-acetylated version had no activity on this target.

D) GALENIC

Various formulations are described below. Additional cosmetic active ingredients, if appropriate in support and/or in addition to the activity of the active ingredient according to the invention, may be added in the appropriate phase according to their hydrophobic or hydrophilic nature. These ingredients can be of any category according to their function(s), the place of application (body, face, neck, bust, hands, hair, eyelashes, eyebrows, hair, etc.) and targeted consumer, for example anti-oxidant, moisturizing, nourishing, protective, smoothing, remodeling, volumizing (lipofiling), acting on the shine of the complexion, against the spots, anti dark circles, anti-glycation, myorelaxing, anti-redness, anti-stretch marks, etc. They are mentioned above in the description.

1) Cream Form, for Example an Antiaging Day Cream for the Face

| Ingredient (INCI name) | Weight % |
| --- | --- |
| Phase A | |
| Sorbitan Stearate | 3.00 |
| Cyclopentasiloxane (and) Cyclohexasiloxane | 2.00 |
| Ethylhexyl Palmitate | 3.00 |

-continued

| Ingredient (INCI name) | Weight % |
|---|---|
| Glyceryl Stearate (and) PEG-100 Stearate | 3.00 |
| Ethylhexyl Methoxycinnamate | 1.00 |
| Ethylhexyl Dimethyl PABA | 1.00 |
| Phase B | |
| Demineralized water | Qsp 100 |
| Ultrez 10 (Carbomer) | 0.40 |
| Phase C | |
| Glycerin | 5.00 |
| Preservative | qs |
| Phase D | |
| Peptide according to the invention in a fatty excipient | 3.00 |
| Phase E | |
| Potassium Sorbate | 0.10 |
| Phase F | |
| Sodium Hydroxide 30% | 0.60 |
| Demineralized water | 6.00 |
| Phase G | |
| Perfume | 0.10 |

Protocol: Weigh phase A and heat it at 75° C. in a water bath. Weigh phase B and let it swell for 20 minutes. Melt phase C until dissolved and add it to phase B. Heat phase (B+C) at 75° C. in a water bath. Pour phase A into the phase (B+C) under Staro stirring. Extemporaneously add phase D to phase (A+B+C). At about 45° C. add phase E and neutralize with phase F. Homogenize well. At 35° C., add phase G. Homogenize well. PH: 6.20.

Example of Ingredients that can be Added to this Formulation:
- CALMOSENSINE™: soothing active for sensitive skins comprising the Tyr-Arg lipo-dipeptide. It reduces discomfort feelings.
- SEBULESS™: purifying sebo-regulator ingredient comprising a *Syringa vulgaris* extract, which mattifies and refreshes complexion, fades the inflammatory blemishes.
- PRODIZIA™: active ingredient comprising an extract of *Albizia julibrissin*, fighting the signs cutaneous fatigue: dark circles, under eye bags, dull complexion and drawn features, by repairing and protection the skin against the caused by damages of glycation and glycoxydation.
- PACIFEEL™: active ingredient comprising a natural extract of the *Mirabilis jalapa* plant also known as the Marvel of Peru, which alleviates cutaneous discomfort, fades redness of sensitive and reactive skin and strengthens and hydrates the epidermis.
- MAJESTEM™: active agent based on plant cells obtained by in vitro cell culture titrated in leontopodic acid; tightens the sagging neck skin, lifts the cheeks smoothes out wrinkles around the eyes, especially crow's feet wrinkles.

2) Gel Form, for Example a Firming Gel for the Body

| Ingredient (INCI name) | Weight % |
|---|---|
| Phase A | |
| Demineralized water | Qsp 100 |
| Ultrez 10 (Carbomer) | 0.20 |
| Phase B | |
| PEG 400 | 5.00 |
| Preservatives | qs |
| Phase C | |
| Dimethicone | 4.00 |
| Pemulen TR2 (Acrylates/C10-30 Alkyl Acrylate Cross Polymer) | 0.20 |
| Phase D | |
| Tween 20 (Polysorbate 20) | 1.00 |
| Peptide of the invention in a fatty excipient | 2.00 |
| Phase E | |
| Potassium Sorbate | 0.10 |
| Phase F | |
| Sodium hydroxide 30% | 0.60 |
| Demineralized water | 5.00 |
| Phase G | |
| Perfume | 0.10 |

Protocol: Disperse Ultrez 10 in water and let it swell for 15 minutes. Heat phase B until dissolved and add it to phase A. Weigh and mix phase C. Mix phase D and add it to phase C; homogenize thoroughly. Add phase (C+D) to phase (A+B). Then add phase E. Leave to swell for 1 hour. Homogenize thoroughly. Neutralize with phase F. Finally, add phase G. pH: 6.10.

Example of Ingredients that can be Added to this Formulation:
- AQUALANCE™: osmo-protector moisturising active ingredient comprising homarine and erythritol.
- LEGANCE™: anti-aging active marketed by Sederma, corresponding to a *Zingiber zerumbet Smith* extract obtained by $CO_2$ supercritical in a water-soluble excipient and titrated in zerumbone ingredient. It is a global anti-aging ingredient for legs. It improves their appearance and comfort by reducing water retention, improving microcirculation and refining adipose tissue.
- BODYFIT™: slimming/firming active ingredient comprising glaucine marketed by Sederma. BODYFIT™ reduces the appearance of cellulite and helps to improve drainage and water distribution in the tissues.
- JUVINITY™: active marketed by Sederma reducing signs of aging on the face and neckline, smoothing wrinkles, densifying and restructuring the dermis.

3) Compact Powder Form

| Ingredient (INCI name) | Weight % |
|---|---|
| Phase A | |
| Talc | Qsp 100 |
| Kaolin | 2.00 |
| Calcium Stearate | 1.00 |
| Mica | 4.00 |
| Silica | 1.00 |
| Bismuth Oxychloride | 2.00 |
| Potassium Sorbate | qs |
| Phenoxyethanol | qs |
| Phase B | |
| Unipure Black LC 989 HLC [CI 77499 (and) Hydrogenated Lecithin] | 0.20 |
| Unipure Red LC 381 HLC [CI 77491 (and) Hydrogenated Lecithin] | 0.60 |

-continued

| Ingredient (INCI name) | Weight % |
|---|---|
| Unipure Yellow LC 182 HLC [CI 77492 (and) Hydrogenated Lecithin] | 1.00 |
| Covapearl Star Gold 2302 AS [CI 77891 (and) CI 77491 (and) Synthetic Fluorphlogopite (and) Triethoxycaprylylsilane] | 0.50 |
| Covapearl Brown 838 HLC [CI 77491 (and) Mica (and) Hydrogenated Lecithin) | 1.00 |
| Covapearl Dark Blue 637 [CI 77510 (&) CI 77891 (&) Mica] | 0.10 |
| Phase C | |
| Crodamol PTIS-LQ-(MV) [Pentaerythrityl Tetraisostearate] | 4.00 |
| Peptide of the invention in a fatty matrix | 3.00 |
| Phase D | |
| Perfume | 0.30 |

Protocol: Weigh phase A and mix. Weigh phase B and pour it into phase B. Pour A+B into the mixer and mix. Add phase C to A+B in several times and mix each time. Add phase D. Check homogeneity at each step.

Example of Ingredients that can be Added to this Formulation:

VEGESOME MOIST 24™: ingredient marketed by SEDERMA designed for the formulation of moisturizing powder makeup ; it is a powder consisting of hollow particles 25 microns (*Lycopodium clavatum* exins) loaded with an *Imperata cylindrica* extract having moisturizing properties.

4) Other Cream Form (Face or Body)

| Ingredient (INCI name) | Weight % |
|---|---|
| Phase A | |
| Arlacel 170 (Glyceryl Stearate (and) PEG-100 Stearate) | 5.50 |
| Abil Wax 2434 (Stearoxy Dimethicone) | 3.00 |
| Acetulan (Cetyl Acetate (and) Acetylated Lanolin Alcohol) | 1.50 |
| Crodacol C 90 (Cetyl Alcohol) | 1.50 |
| Mineral Oil | 3.00 |
| Shea Butter | 5.00 |
| Unsaponifiable Shea | 1.00 |
| Parsol MCX (Ethylhexyl Methoxicinnamate) | 3.50 |
| Phase B | |
| Demineralized water | Qs 100 |
| Phase C | |
| Carbopol 940 (Carbomer) | 0.20 |

| Ingredient (INCI name) | Weight % |
|---|---|
| Phase D | |
| Demineralized water | 2.00 |
| Triethanolamine 99% | 0.20 |
| Phase E | |
| Propylene Glycol | 0.10 |
| Mixed Parabens | |
| Phase F | |
| Sodium Hydroxide 30% | 5.00 |
| Demineralized water | qs |
| Phase G | |
| Peptide according to the invention in an hydrophilic matric | 2.00 |

Protocol: Weigh phase A and heat it at 75° C. in a water bath. Weigh phase B and let it swell for 20 minutes. Melt phase C until dissolved and add it to phase B. Heat phase (B+C) at 75° C. using a water bath. Pour phase A into the (B+C) phase under Staro stirring. Extemporaneously add phase D to phase (A+B+C). At about 45° C. add phase E and neutralize with phase F. Homogenize well. At 35° C., add phase G. Homogenize well. PH: 6.20.

Example of Ingredients that can be Added to this Formulation:

SUBLISKIN™: active ingredient that moisturizes and smooths the skin while allowing it to resist to external aggressions.

VENUCEANE™: active marketed by Sederma comprising a *Thermus thermophiles* biotechnological extract, that prevents visible signs of photo-aging (spots, wrinkles, dryness . . . ), protects cell structures from damages caused by UV and strengthens skin integrity.

KOMBUCHKA™: active ingredient acting on complexion marketed by Sederma.

INTENSLIM™: slimming active ingredient marketed by Sederma corresponding to a synergistic combination of extracts obtained by *Globularia cordifolia* plant cell culture, *Zingiber zerumbet Smith* titrated in zerumbone and vegetable caffeine obtained by supercritical $CO_2$ extraction.

CITYSTEM™: active ingredient based on plant cells obtained in vitro from *Marrubium vulgare* with a high concentration of Forsythoside B; used against the attacks of pollution: makes the skin soft and smooth, refines the skin texture, reduces the visibility of comedones, leaving the skin radiant and purified.

The invention claimed is:

1. A peptide having a length of from 3 to 6 amino acids and which comprises at least one peptide sequence K*(Ac)GH or K*(Ac)HG, wherein K* is selected from the group consisting of lysine, ornithine, diaminobutyric acid, diaminopropionic acid, and a hydroxylated derivative thereof;

K*(Ac) represents a lysine, ornithine, diaminobutyric acid, diaminopropionic acid or a hydroxylated derivative thereof, which is acetylated on the amine of the lateral hydrocarbon chain thereof;

the amino acids of the peptide other than K*(Ac)GH or K*(Ac)HG, when present, are each independently selected from the group consisting of lysine, histidine, glycine, alanine, and K*;

the peptide is modified at the N-terminal with a modification selected from the group consisting of —CO—$R_1$ and —$SO_2$—$R_1$; and/or the peptide is modified at the C-terminal with a modification selected from the group consisting of —$OR_1$, —$NH_1$, —$NH_1R_2$, and —$NR_1R_2$; and $R_1$ and $R_2$, when present, independently of one another, are chosen from an alkyl, aryl, aralkyl, alkylaryl, alkoxy and aryloxy group, which is linear, branched, cyclic, polycyclic, unsaturated, hydroxylated, carbonylated, phosphorylated and/or sulfurated, said group having from 1 to 24 carbon atoms and may optionally have in its carbon backbone an O, S and/or N heteroatom.

2. The peptide of claim 1, wherein K* is lysine and K*(Ac) represents an s-acetylated lysine.

3. The peptide of claim 1, wherein the $R_1$ and/or $R_2$ group comprises from 3 to 24 carbon atoms.

4. The peptide of claim 1, which is modified at the N-terminal with —CO-$R_1$.

5. The peptide of claim 4, wherein —CO—$R_1$ is an octanoyl, decanoyl, lauroyl, myristoyl, palmitoyl, stearoyl, biotinoyl, elaidoyl, oleoyl or lipoyl group.

6. The peptide of claim 1, which is modified at the N-terminal and not modified at the C terminal.

7. The peptide of claim 1, represented by the formula (1) or (2):

$$X-K^*(Ac)GH-Z \quad (1)$$

$$\text{or } X-K^*(Ac)HG-Z \quad (2)$$

wherein
X represents, when present, the modification at the N-terminal, and
Z represents, when present, the modification at the C-terminal.

8. The peptide of claim 7, which is Pal-K(Ac)GH or Pal-K(Ac)HG.

9. A cosmetic composition comprising as an active ingredient an effective amount of at least one peptide of claim 1 in a physiologically acceptable medium.

10. The composition of claim 9, further comprising at least one additional active ingredient selected from the group consisting of vitamin B3 compounds, niacinamide, tocopherol, retinoid compounds, hexamidine, a-lipoic acid, resveratrol, DHEA, hyaluronic acid, and peptides.

11. A method for a non-therapeutic cosmetic treatment to improve the general condition of the skin and/or its appendages and to treat their imperfections, comprising applying to the skin and/or its appendages at least one peptide of claim 1.

12. The method of claim 11, wherein the at least one peptide is applied topically to the skin and/or its appendages.

13. The method of claim 11, wherein the non-therapeutic cosmetic treatment is an anti-aging treatment of the skin and/or its appendages.

14. The method of claim 13, wherein the anti-aging treatment is for a treatment:
of wrinkles and fine lines; and/or
for improving the mechanical properties of the skin; and/or
for increasing the density and volume of the skin; and/or
for fighting stretch marks; and/or
for improving the homogeneity and/or radiance of complexion.

15. The method of claim 11, further comprising applying to the skin and/or its appendages at least one additional active ingredient selected from the group consisting of vitamin B3 compounds, niacinamide, tocopherol, retinoid compounds, hexamidine, a-lipoic acid, resveratrol, DHEA, hyaluronic acid, and peptides.

* * * * *

SEQUENCE LISTING

```
<160> NUMBER OF SEQ ID NOS: 25

<210> SEQ ID NO 1
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
```

```
<400> SEQUENCE: 1

Lys Thr Thr Lys Ser
1               5

<210> SEQ ID NO 2
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 2

Gly Gln Pro Arg
1

<210> SEQ ID NO 3
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 3

Val Gly Val Ala Pro Gly
1               5

<210> SEQ ID NO 4
<211> LENGTH: 4
<212> TYPE: PRT
<213> ORGANISM: artificial sequence
<220> FEATURE:
<223> OTHER INFORMATION: synthetic peptide

<400> SEQUENCE: 4

Arg Ser Arg Lys
1

<210> SEQ ID NO 5
<211> LENGTH: 4
<212> TYPE: PRT
<213> ORGANISM: artificial sequence
<220> FEATURE:
<223> OTHER INFORMATION: synthetic peptide

<400> SEQUENCE: 5

Gly Gln Pro Arg
1

<210> SEQ ID NO 6
<211> LENGTH: 4
<212> TYPE: PRT
<213> ORGANISM: artificial sequence
<220> FEATURE:
<223> OTHER INFORMATION: synthetic peptide

<400> SEQUENCE: 6

Lys Thr Phe Lys
1
```

```
<210> SEQ ID NO 7
<211> LENGTH: 4
<212> TYPE: PRT
<213> ORGANISM: Artificial sequence
<220> FEATURE:
<223> OTHER INFORMATION: Synthetic peptide

<400> SEQUENCE: 7

Lys Thr Ala Lys
1

<210> SEQ ID NO 8
<211> LENGTH: 4
<212> TYPE: PRT
<213> ORGANISM: Artificial sequence
<220> FEATURE:
<223> OTHER INFORMATION: Synthetic peptide

<400> SEQUENCE: 8

Lys Ala Tyr Lys
1

<210> SEQ ID NO 9
<211> LENGTH: 4
<212> TYPE: PRT
<213> ORGANISM: Artificial sequence
<220> FEATURE:
<223> OTHER INFORMATION: Synthetic peptide

<400> SEQUENCE: 9

Lys Phe Tyr Lys
1

<210> SEQ ID NO 10
<211> LENGTH: 5
<212> TYPE: PRT
<213> ORGANISM: artificial sequence
<220> FEATURE:
<223> OTHER INFORMATION: synthetic peptide

<400> SEQUENCE: 10

Lys Thr Thr Lys Ser
1               5

<210> SEQ ID NO 11
<211> LENGTH: 6
<212> TYPE: PRT
<213> ORGANISM: artificial sequence
<220> FEATURE:
<223> OTHER INFORMATION: Synthetic peptide

<400> SEQUENCE: 11

Gly Lys Thr Thr Lys Ser
1               5

<210> SEQ ID NO 12
<211> LENGTH: 6
<212> TYPE: PRT
<213> ORGANISM: artificial sequence
<220> FEATURE:
<223> OTHER INFORMATION: synthetic peptide

<400> SEQUENCE: 12

Val Gly Val Ala Pro Gly
1               5
```

-continued

```
<210> SEQ ID NO 13
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 13

Lys Thr Phe Lys
1

<210> SEQ ID NO 14
<211> LENGTH: 4
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 14

Lys Thr Phe Lys
1

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 15

Lys Thr Ala Lys
1

<210> SEQ ID NO 16
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 16

Lys Ala Tyr Lys
1

<210> SEQ ID NO 17
<211> LENGTH: 4
<212> TYPE: PRT
<213> ORGANISM: Artificial sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 17

Lys Phe Tyr Lys
1

<210> SEQ ID NO 18
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (5)..(5)
<223> OTHER INFORMATION: Xaa being either a Proline P or a Leucine L.

<400> SEQUENCE: 18

Tyr Gly Gly Phe Xaa
1               5

<210> SEQ ID NO 19
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (6)..(6)
<223> OTHER INFORMATION: Xaa being Trp, Phe, Tyr, Tic, 7-hydroxy-Tic or
      Tpi

<400> SEQUENCE: 19

His Leu Asp Ile Ile Xaa
1               5

<210> SEQ ID NO 20
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 20

Gly Lys Thr Thr Lys Ser
1               5

<210> SEQ ID NO 21
<211> LENGTH: 6
<212> TYPE: PRT
<213> ORGANISM: artificial sequence
```

```
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation on the N-terminal end

<400> SEQUENCE: 21

Glu Glu Met Gln Arg Arg
1               5

<210> SEQ ID NO 22
<211> LENGTH: 5
<212> TYPE: PRT
<213> ORGANISM: artificial sequence
<220> FEATURE:
<223> OTHER INFORMATION: synthetic peptide

<400> SEQUENCE: 22

Tyr Ala Gly Phe Leu
1               5

<210> SEQ ID NO 23
<211> LENGTH: 4
<212> TYPE: PRT
<213> ORGANISM: artificial sequence
<220> FEATURE:
<223> OTHER INFORMATION: synthetic peptide

<400> SEQUENCE: 23

Ala His Ser His
1

<210> SEQ ID NO 24
<211> LENGTH: 6
<212> TYPE: PRT
<213> ORGANISM: artificial sequence
<220> FEATURE:
<223> OTHER INFORMATION: synthetic peptide

<400> SEQUENCE: 24

Ser Ile Lys Val Ala Val
1               5

<210> SEQ ID NO 25
<211> LENGTH: 6
<212> TYPE: PRT
<213> ORGANISM: artificial sequence
<220> FEATURE:
<223> OTHER INFORMATION: synthetic peptide

<400> SEQUENCE: 25

Gly Pro Gln Gly Pro Gln
1               5
```